US009625406B2

(12) United States Patent
Zanella, Sr.

(10) Patent No.: US 9,625,406 B2
(45) Date of Patent: Apr. 18, 2017

(54) COMBUSTIBLE GAS SENSORS INCLUDING INTEGRAL SUPPORT STRUCTURES AND COMBUSTIBLE GAS SENSOR WITH MULTIPLE ACTIVE ELEMENTS

(71) Applicant: MSA TECHNOLOGY, LLC., Cranberry Township, PA (US)

(72) Inventor: Mark Flori Zanella, Sr., Chicora, PA (US)

(73) Assignee: MSA TECHNOLOGY, LLC, Cranberry Township, PA (US)

( * ) Notice: Subject to any disclaimer, the term of this patent is extended or adjusted under 35 U.S.C. 154(b) by 429 days.

(21) Appl. No.: 14/454,119

(22) Filed: Aug. 7, 2014

(65) Prior Publication Data

US 2014/0348709 A1    Nov. 27, 2014

Related U.S. Application Data

(62) Division of application No. 12/916,370, filed on Oct. 29, 2010, now Pat. No. 8,826,721.

(Continued)

(51) Int. Cl.
*G01N 27/16* (2006.01)
*G01N 33/00* (2006.01)

(52) U.S. Cl.
CPC ......... *G01N 27/16* (2013.01); *G01N 33/0016* (2013.01); *G01N 33/0027* (2013.01); *G01N 33/0031* (2013.01); *G01N 33/0073* (2013.01)

(58) Field of Classification Search
CPC .............. G01N 27/16; G01N 33/0009; G01N 33/0016; G01N 33/0027; G01N 33/0031;

(Continued)

(56) References Cited

U.S. PATENT DOCUMENTS 4,533,520 A    8/1985 Bossart
4,981,369 A *  1/1991 Kumada ............... G01N 27/18
                                                 374/10

(Continued)

FOREIGN PATENT DOCUMENTS

EP    0311964 A2    4/1989
EP    0313390 A2    4/1989

(Continued)

OTHER PUBLICATIONS

English translation of office action issued in counterpart Japanese patent application No. 2012-537151.

(Continued)

*Primary Examiner* — Blake A Tankersley
(74) *Attorney, Agent, or Firm* — Bartony & Associates, LLC (57) ABSTRACT

A combustible gas sensor includes at least a first sensing element comprising a first conductive element having, for example, an average diameter less than 20 μm in electrical connection with electronic circuitry. The combustible gas sensor further includes a first support element having a first anchored end, a second anchored end and an extending intermediate section between the first anchored end and the second anchored end, the extending intermediate section providing support for the first conductive element. Another combustible gas sensor includes a first sensing element and a second sensing element. The first sensing element includes a first catalyst support member having a volume less than a sphere having a diameter of 500 μm. The second sensing element includes a second catalyst support member having a volume less than a sphere having a diameter of 500 μm. The combustible gas sensor further includes electronic circuitry that is adapted to cycle between a first mode in which the first sensing element is operated in a higher power mode and the second sensing element is operated in a lower power (Continued)

mode and a second mode in which the second sensing element is operated in a higher power mode and the first sensing element is operated in a lower power mode.

16 Claims, 6 Drawing Sheets

Related U.S. Application Data (60) Provisional application No. 61/256,749, filed on Oct. 30, 2009.

(58) Field of Classification Search
CPC .......... G01N 33/0032; G01N 33/0062; G01N 33/0073
See application file for complete search history.

(56) References Cited

U.S. PATENT DOCUMENTS

| | | |
|---|---|---|
| 5,599,584 A | 2/1997 | Champney, Jr. |
| 5,780,715 A | 7/1998 | Imblum |
| 6,344,174 B1 | 2/2002 | Miller |
| 6,663,834 B1 | 12/2003 | Miller |
| 6,705,152 B2 | 3/2004 | Routkevitch |
| 2002/0020208 A1* | 2/2002 | Slater .................... G01N 27/16 73/23.31 |
| 2004/0208789 A1 | 10/2004 | Miller |
| 2005/0217370 A1 | 10/2005 | Takahashi |
| 2006/0228261 A1 | 10/2006 | Iwamoto |
| 2008/0226505 A1* | 9/2008 | Willettt .................. G01N 27/16 422/98 |

FOREIGN PATENT DOCUMENTS

| | | |
|---|---|---|
| EP | 0364982 A2 | 4/1990 |
| EP | 1505385 A1 | 2/2005 |
| JP | H08247984 | 9/1996 |
| JP | 2008096267 | 4/2008 |
| WO | WO0043765 A1 | 7/2000 |
| WO | WO2006111727 A1 | 10/2006 |
| WO | WO2011053866 A1 | 5/2011 |

OTHER PUBLICATIONS

Mosely, P.T. and Tofield, B.C., ed., Solid State Gas Sensors, Adams Hilger Press, Bristol, England, 18-31 (1987).
Firth, J.G. et al., The Principles of the Detection of Flammable Atmospheres by Catalytic Devices, Combustion and Flame 21, 303-311 (1973).
Cullis, C.F., and Firth, J.G., Eds., Detection and Measurement of Hazardous Gases, Heinemann, Exeter, 29-67 (1981).

\* cited by examiner

COMBUSTIBLE GAS SENSORS INCLUDING INTEGRAL SUPPORT STRUCTURES AND COMBUSTIBLE GAS SENSOR WITH MULTIPLE ACTIVE ELEMENTS

CROSS-REFERENCE TO RELATED APPLICATION

This application is a divisional patent application of U.S. patent application Ser. No. 12/916,370, filed Oct. 29, 2010, which claims benefit of U.S. Provisional Patent Application Ser. No. 61/256,749, filed Oct. 30, 2009, the disclosures of which are incorporated herein by reference.

BACKGROUND

The terms used herein are not intended to be limited to any particular narrow interpretation unless clearly stated otherwise in this document. References set forth herein may facilitate understanding of the devices, systems and/or methods or the background. The disclosure of any reference cited herein is incorporated by reference.

Figure 1A:
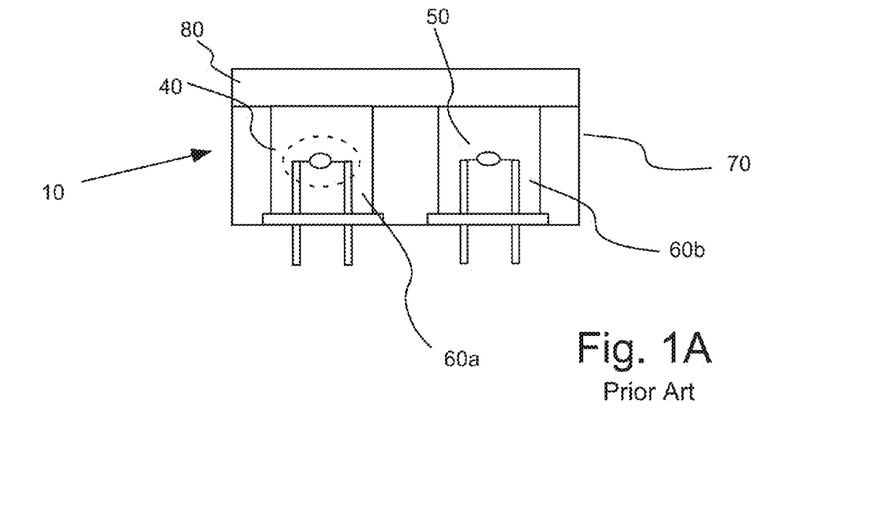
FIG. 1A illustrates an embodiment of a currently available combustible gas sensor.
Figure 1B:
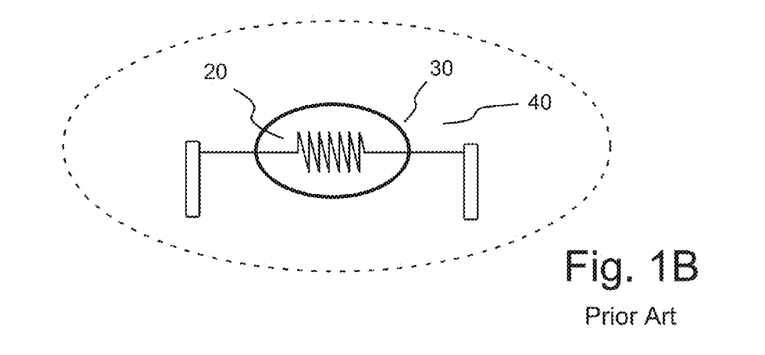
FIG. 1B illustrates an enlarged view of the active sensing element, pelement or detector of the combustible gas sensor of FIG. 1A.

Catalytic or combustible (flammable) gas sensors have been in use for many years to, for example, prevent accidents caused by the explosion of combustible or flammable gases. In general, combustible gas sensors operate by catalytic oxidation of combustible gases. As illustrated in FIGS. 1A and 1B, a conventional combustible gas sensor 10 typically includes an element such as a platinum element wire or coil 20 encased in a refractory (for example, alumina) bead 30, which is impregnated with a catalyst (for example, palladium or platinum) to form an active or sensing element, which is sometimes referred to as a pelement 40, pellistor, detector or sensing element. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Bead 30 will react to phenomena other than catalytic oxidation that can change its output (i.e., anything that changes the energy balance on the bead) and thereby create errors in the measurement of combustible gas concentration. Among these phenomena are changes in ambient temperature, humidity and pressure.

Figure 1C:
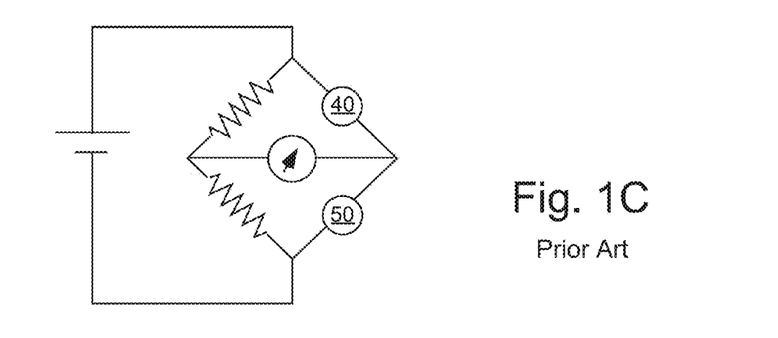
FIG. 1C illustrates an embodiment of the circuitry of the combustible gas sensor of FIG. 1A.

To minimize the impact of secondary effects on sensor output, the rate of oxidation of the combustible gas may be measured in terms of the variation in resistance of sensing element or pelement 40 relative to a reference resistance embodied in an inactive, compensating element or pelement 50. The two resistances are typically part of a measurement circuit such as a Wheatstone bridge circuit as illustrated in FIG. 1C. The output or the voltage developed across the bridge circuit when a combustible gas is present provides a measure of the concentration of the combustible gas. The characteristics of compensating pelement 50 are typically matched as closely as possible with active or sensing pelement 40. Compensating pelement 50, however, typically either carries no catalyst or carries an inactivated/poisoned catalyst.

Active or sensing pelement 40 and compensating pelement 50 can, for example, be deployed within wells 60*a* and 60*b* of an explosion-proof housing 70 and can be separated from the surrounding environment by a flashback arrestor, for example, a porous metal frit 80. Porous metal frit 80 allows ambient gases to pass into housing 70 but prevents ignition of flammable gas in the surrounding environment by the hot elements. Such catalytic gas sensors are usually mounted in instruments which, in some cases, must be portable and, therefore, carry their own power supply. It is, therefore, desirable to minimize the power consumption of a catalytic gas sensor.

Electrical power dissipation of catalytic gas sensors as illustrated in FIGS. 1A through 1C is typically on the order of 250 to 700 mW. Further, the catalytic element or pelement and the compensating element or pelement are expensive to produce. Together, the pair typically accounts for well over half of the cost to manufacture the catalytic gas sensor. Further, the compensating element, which must closely match the sensing element in size and environmental responses, accounts for nearly half of the sensor power and half the cost of the sensing element/compensating element pair. Substantial research effort has been devoted to the development of low power combustible gas detectors and to reducing the costs of or eliminating the compensating element. U.S. Pat. No. 6,663,834, for example, discloses a combustible gas sensor in which the compensating element is replaced electronically by a thermistor network to compensate for changes in ambient temperature. The power requirements of the sensor of U.S. Pat. No. 6,663,834, however, remain relatively high.

Reducing the size of the sensing element wire and catalyst support bead of the sensing element can reduce the power requirements of a combustible gas sensor. Decreased wire diameter is generally associated with higher resistance and thus lower current/power to achieve a certain operating temperature. Moreover, reducing the size/volume of the sensing element/pelement reduces the effects of humidity and pressure changes on the sensor. In the past, sensors included elements made from wires of ample size and strength to support themselves. As the technology advanced over the years, efforts were made to reduce the power levels required to operate the sensors by, for example, reducing the size of the sensing element. Whereas early combustible gas sensors required more than a watt of power for operation, recently available combustible gas sensors have been able to operate in the 200-300 milliwatt range.

Reducing element size has, however, required the incorporation of some form of mechanical support for the smaller diameter, more fragile sensing elements and/or wires. Common mechanical supports have included various packing methods, or the use of a third support post.

Unfortunately, such mechanical supports draw or conduct heat away from the sensing (and/or compensating) element and thus result in higher power requirements to operate the element at a particular range of temperature.

SUMMARY

In one aspect, a combustible gas sensor includes at least a first sensing element including a first conductive element having a diameter less than 20 μm in electrical connection with electronic circuitry. The combustible gas sensor further includes a first support element exhibiting a quotient calculated by dividing a tensile strength thereof in units of pounds per square inch or psi by a thermal conductivity thereof in units of watts/cm/° C. of at least 250,000. The first support element is in operative connection with the first conductive element to provide support therefor. The first support element can, for example, contacts the first conductive element to provide support therefor.

In another aspect, a combustible gas sensor includes at least a first sensing element comprising a first conductive element having, for example, an average diameter less than 20 μm in electrical connection with electronic circuitry. The combustible gas sensor further includes a first support element having a first anchored end, a second anchored end and an extending intermediate section between the first anchored end and the second anchored end, the extending intermediate section providing support for the first conductive element.

The first support element can, for example, be in operative connection with the first conductive element to provide support therefor. The first support element can, for example, contact the first conductive element to provide support therefor. The first support element can, for example, exhibit a quotient calculated by dividing a tensile strength thereof in units of pounds per square inch or psi by a thermal conductivity thereof in units of watts/cm/° C. of at least 250,000.

The first conductive element can, for example, have a diameter less than 12.5 μm. In several embodiments, the first conductive element wire has a diameter no greater than approximately 10 μm.

In a number of embodiments, the combustible gas sensor includes a first support member to which the first anchored end of the first support element is anchored or attached and a second support member to which the second anchored end of the first support element is anchored or attached.

The combustible gas sensor can also include a first catalyst support member in operative connection with the first conductive element, wherein the intermediate section of the first support element contacts the first catalyst support member to provide support for the first conductive element. In a number of embodiments, the first support element passes through at least a portion of the first catalyst support. The first catalyst support member supports a catalyst thereon. In a number of embodiments, the first catalyst support member has a volume less than a sphere having a diameter of 500 μm (wherein the volume of a sphere is calculated by the formula $4/3 \times \pi \times (D/2)^3$). The first catalyst support member can have a volume no greater than a sphere having a diameter of no greater than 440 μm, or a diameter no greater than 300 μm.

The combustible gas sensor can further include at least two electrically conductive contact members between which the first conductive element is connected. The contact members are in electrical connection with electronic circuitry.

The first support element can, for example, include an alloy of at least one of tungsten, nickel, molybdenum or titanium with at least one of platinum, palladium, rhodium or iridium. In several embodiments, the first support element includes a platinum-tungsten alloy.

The first support element can, for example, have an average diameter in the range of approximately 0.0005 inches to approximately 0.0025 inches. In several embodiments, the first support element has an average diameter of approximately 0.001 inches.

In several embodiments, the first conductive element includes a platinum-iridium alloy or a platinum-rhodium alloy.

In a number of embodiments, the first conductive element has an average diameter no greater than approximately 10 μm.

The first support element can, for example, have a tensile strength of at least 100,000 psi, at least 250,000 psi or at least 500,000 psi. The first support element can, for example, have a thermal conductivity of no greater than 0.5 watts/cm/° C., no greater than 0.25 watts/cm/° C. or no greater than 0.10 watts/cm/° C.

The combustible gas sensor can further include at least a second sensing element including a second conductive element having, for example, an average diameter less than 20 μm in electrical connection with the electronic circuitry. The combustible gas sensor can further include a second support element second support element including a first anchored end, a second anchored end and an extending intermediate section between the first anchored end and the second anchored end. The extending intermediate section of the second support element provides support for the second conductive element. The second support element can, for example, be in operative connection with the second conductive element to provide support therefor. The second support element can, for example, contact the second conductive element to provide support therefor. The second support element can, for example, exhibit a quotient calculated by dividing a tensile strength thereof in units of pounds per square inch or psi by a thermal conductivity thereof in units of watts/cm/° C. of at least 250,000.

The combustible gas sensor can further include a third support member to which the first anchored end of the second support element is anchored and a fourth support member to which the second anchored end of the first support element is anchored.

The combustible gas sensor can also include a second catalyst support member in operative connection with the second conductive element, wherein the intermediate section of the second support element contacts the second catalyst support member to provide support for the second conductive element. The second support element can, for example, pass through at least a portion of the second catalyst support. The second catalyst support member supports a catalyst thereon.

The second catalyst support member can, for example, have a volume less than a sphere having a diameter of 500 μm, a volume no great than a sphere having a diameter of no greater than 440 μm or a volume no greater than a sphere having a diameter of no greater than 300 μm.

The combustible gas sensor can further include at least two electrically conductive contact members between which the second conductive element is connected. The contact members are in electrical connection with the electronic circuitry.

The second support element can, for example, include an alloy of at least one of tungsten, nickel, molybdenum or titanium with at least one of platinum, palladium or rhodium. In several embodiments, the second support element includes a platinum-tungsten alloy.

In a number of embodiments, the second support element has an average diameter in the range of approximately 0.0005 inches to approximately 0.0025 inches. The second support element can, for example, have an average diameter of approximately 0.001 inches.

The second conductive element can, for example, include a platinum-iridium alloy or a platinum-rhodium alloy.

In several embodiments, the second conductive element has an average diameter no greater than approximately 10 μm.

The second support element can, for example, have a tensile strength of at least 100,000 psi, at least 250,000 psi, or at least 500,000 psi. The second support element can, for example, have a thermal conductivity of no greater than 0.50 watts/cm/° C., no greater than 0.25 watts/cm/° C. or no greater than 0.10 watts/cm/° C.

The electronic circuitry can, for example, be adapted to or be operable to cycle between a first mode in which the first sensing element is operated in a higher power mode and the second sensing element is operated in a lower power mode and a second mode in which the second sensing element is operated in a higher power mode and the first sensing element is operated in a lower power mode.

In the first mode, the second sensing element can, for example, be used to compensate for ambient temperature changes. In the second mode, the first sensing element can, for example, be used to compensate for ambient temperature changes.

The electronic circuitry can, for example, be adapted to periodically switch between the first mode and the second mode. The electronic circuitry can, for example, be adapted to switch between the first mode and the second mode upon a manually controlled event. The manually controlled event can, for example, include a power on event.

In another aspect, a combustible gas sensor includes a first sensing element and a second sensing element. The first sensing element includes a first catalyst support member having a volume less than a sphere having a diameter of 500 μm. The second sensing element includes a second catalyst support member having a volume less than a sphere having a diameter of 500 μm. The combustible gas sensor further includes electronic circuitry that is adapted to cycle between a first mode in which the first sensing element is operated in a higher power mode and the second sensing element is operated in a lower power mode and a second mode in which the second sensing element is operated in a higher power mode and the first sensing element is operated in a lower power mode.

In the first mode, the second sensing element can, for example, be used to compensate for ambient temperature changes. In the second mode, the first sensing element can, for example, be used to compensate for ambient temperature changes.

The first sensing element can, for example, include a first conductive element having an average diameter less than 20 μm of less than 12.5 μm in electrical connection with the electronic circuitry. In a number of embodiments, the first conductive element has an average diameter of no greater than approximately 10 μm. The combustible gas sensor can further include a first support element as described above. The second sensing element can, for example, include a second conductive element having an average diameter less than 20 μm or no less than 12.5 μm in electrical connection with the electronic circuitry. In a number of embodiments, the second conductive element has an average diameter of no greater than approximately 10 μm. The combustible gas sensor can further include a second support element as described above.

In another aspect, a method of operating a combustible gas sensor, which includes a first sensing element and a second sensing element, wherein the first sensing element includes a first catalyst support member having a volume less than a sphere having a diameter of 500 μm and upon which a catalyst is supported, and wherein the second sensing element includes a second catalyst support member having a volume less than a sphere having a diameter of 500 μm and upon which a catalyst is supported, includes: cycling between a first mode in which the first sensing element is operated in a higher power mode and the second sensing element is operated in a lower power mode and a second mode in which the second sensing element is operated in a higher power mode and the first sensing element is operated in a lower power mode.

In the first mode, the second sensing element can, for example, be used to compensate for ambient temperature changes. In the second mode, the first sensing element can, for example, be used to compensate for ambient temperature changes.

Devices, systems and/or methods described herein, along with the attributes and attendant advantages thereof, will best be appreciated and understood in view of the following detailed description taken in conjunction with the accompanying drawings.

DETAILED DESCRIPTION

As used herein and in the appended claims, the singular forms "a," "an", and "the" include plural references unless the context clearly dictates otherwise. Thus, for example, reference to "a support element" includes a plurality of such support elements and equivalents thereof known to those skilled in the art, and so forth, and reference to "the support element" is a reference to one or more such support elements and equivalents thereof known to those skilled in the art, and so forth.

Figures 2A, 2B:
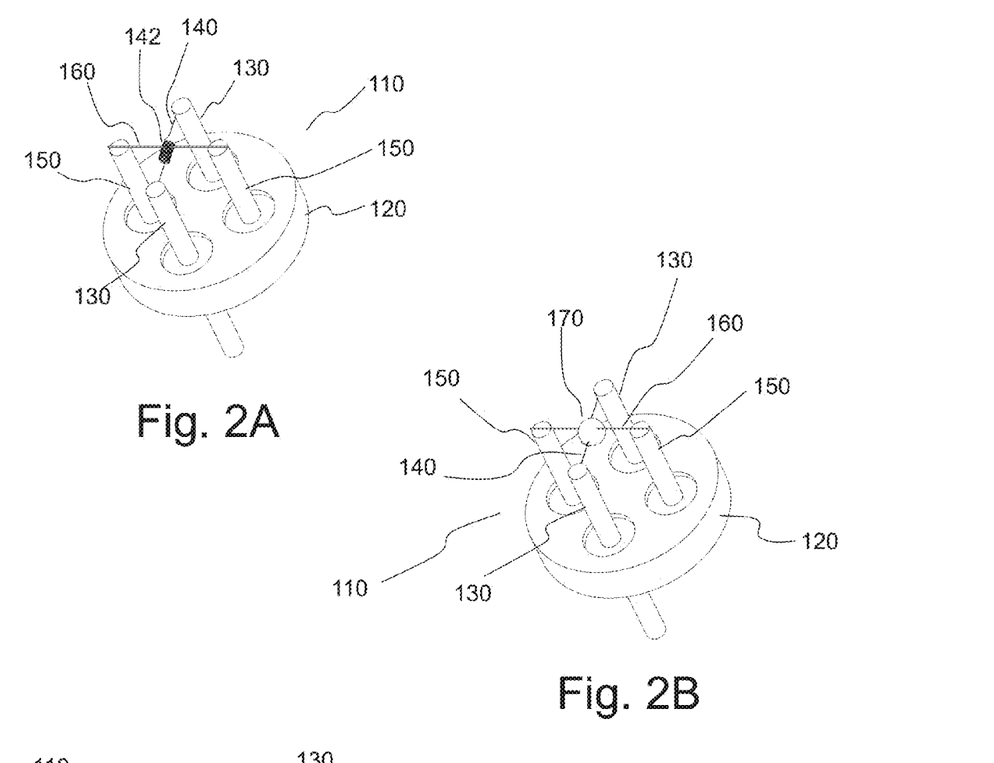
FIG. 2A illustrates a perspective view of an embodiment of a detector assembly wherein a sensing element is supported by a supporting wire.
FIG. 2B illustrates a perspective view of the detector assembly of FIG. 2A including a ceramic bead (upon which a catalyst is supported) formed over the sensing element wire.
Figure 2C:
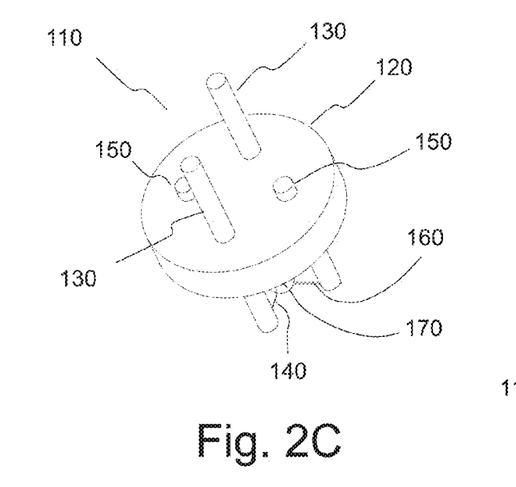
FIG. 2C illustrates another perspective view (generally opposite that of FIG. 2B) of the detector assembly of FIG. 2B.

FIGS. 2A through 2C illustrate an embodiment of a detector assembly 110 (for use, for example, in a gas sensor as illustrated in FIG. 1A). As, for example, illustrated in FIG. 2A, detector assembly 110 includes a base 120 to which two electrically conductive contact members 130 (extending members or posts in the illustrated embodiment) are attached. A sensing conductive element 140 is connected between contact members 130, wherein each end of conductive element 140 is connected to or anchored to one of contact members 130. In the illustrated embodiment of FIG. 2A, conductive element 140 includes an intermediate section including a coiled section 142 that can, for example, be located approximately centrally between the ends of conductive element 140. Detector assembly 110 further includes two support members 150 (extending members or posts in the illustrated embodiment) connected to base 120. In the illustrated embodiment, a support member or element 160 in the form of, for example, a wire, a ribbon, a rod or other suitable support structure or material extends between support members or posts 150. Base 120, contact members 130 and support members 150 can, for example, be formed of a metal such as KOVAR® (a nickel-cobalt ferrous alloy designed to be compatible with the thermal expansion characteristics of borosilicate glass) available from Carpenter Technology Corporation of Reading, Pa. Contact members 130 and support members 150 can, for example, be sealed to base 120 using a glass such as borosilicate glass to provide electrical isolation.

Although a number of support systems or structures in previously available combustible gas sensor limited bead movement in all 3 planes or dimensions, such support structures required additional operational power to overcome associated heat losses. Using a strong yet relatively thin support element 160 anchored, connected or attached at each end thereof (for example, anchored at two support members or posts 150) prevents bead movement in all three dimensions while limiting heat loss. In the illustrated embodiment of FIG. 2A, support element 160 passes through and contacts one of the coils of coiled section 142. Contact between support element 150 and conductive element 140 is thus minimal. As described below, support element 150 need not contact conductive element 140 to provide support therefor, but can contact or pass through a catalyst support member 170 encompassing conductive element 140.

A number of materials and support structures were studied to adequately support a sensing element while minimizing heat loss from the support member. A number of support elements or structures with low thermal conductivity, such as ceramic rods, were studied, but to obtain adequate strength, larger than desired diameters or cross-section areas were required, resulting in excessive heat loss. In testing a number of metallic support elements (for example, wires or rods), it was discovered a balance can be established between the tensile strength and the thermal conductivity to achieve an effective result. In general, a quotient or ratio calculated by dividing the tensile strength in units of pounds per square inch of psi by the thermal conductivity in units of watts/cm/° C. can, for example, be at least 250,000, at least 400,000 or even at least 500,000. For example, in several studies, a support element in the form of a wire made from an alloy of platinum and tungsten had a tensile strength of 250,000 psi and a thermal conductivity of 0.5 watts/cm/° C., resulting in a quotient of 500,000. For support elements having a higher tensile strength, a higher thermal conductivity may be acceptable since support elements of smaller average diameter (or average cross-sectional area) can be used (resulting in less mass to conduct heat away from the sensing element). For example, in the case of a tungsten support element having a tensile strength of 600,000 psi and a thermal conductivity of 1.27 watts/cm/° C., a smaller average diameter support element can be used to achieve a similar result to that achieved with the platinum-tungsten alloy support element described above. Alternatively, one could also choose a support element of an alloy of platinum with 20% iridium having a larger average diameter. Such a platinum-iridium alloy has a tensile strength of 120,000 psi and a thermal conductivity of 0.18 watts/cm/° C. Metal support elements or metal alloy elements having the above-described properties can be used to maximize strength/support while minimizing heat loss.

In that regard, in several embodiments, support element 160 exhibits relatively high strength (for example, having a tensile strength of at least 100,000 psi, at least 250,000 psi, or even at least 400,000 psi) as well as low thermal conductivity (for example, having a thermal conductivity less than 1.5 less watts/cm/° C., less than 0.5 watts/cm/° C., no greater than 0.25 watts/cm/° C., or even no greater than 0.10 watts/cm/° C.) to provide a quotient as described above. In a number of embodiments, the average diameter of support element 160 (in the case of a support element of a generally circular cross-section) is in the range of approximately 0.0005 to 0.0025 inches. In the case of support elements having a noncircular cross-section, the average cross-sectional area can, for example, be in the range of the average cross-sectional area of an element of generally circular cross-section having an average diameter in the range of approximately 0.0005 to 0.0025 inches. References herein to elements having a certain average diameter are also references to elements having a generally noncircular cross-section, but having an average cross-sectional area equivalent to the average cross-sectional area provided by the stated average diameter. In several representative studies, an in-molded wire was used as support element 160. In several such embodiments, a platinum-tungsten alloy support element 160 having an average diameter of approximately (that is, within 10% of) 0.001 inches provided a robust support, and did not result in measurable additional power required to operate sensing element 140. Alloys of tungsten, nickel, molybdenum or titanium with, for example, platinum, palladium or rhodium can, for example, be used in support element 160. As illustrated in FIG. 2B, catalyst support member 170 (for example, a ceramic bead in a number of embodiments) can be formed on coil section 120 of sensing conductive element 140 to support a catalyst and form a sensing element/pelement. In forming catalyst support member 170 as a ceramic bead, an aluminum oxide suspension was fired onto coiled section 142. The resultant catalyst support member/ceramic bead 170 was impregnated with a catalyst. Although a bare wire comprising a catalytic material (such as platinum) can be used as a sensing element in certain embodiments of a combustible gas sensor, a catalyst support member 170 (such as a ceramic bead) provides increased surface area for one or more catalyst species.

In the embodiment illustrated in FIGS. 2A through 2C, catalyst support member 170 is formed over (to encompass) conductive element 140 and support element 160. In a number of embodiment, support element 160 need not contact conductive element 140 to provide support therefor. For example, support element 160 can pass through or contact catalyst support member 170 without contacting conductive element 140 and indirectly provide support for conductive element 140. To provide support for conductive element 140 in three dimensions, support element 160 preferably passes through catalyst support member 170.

The support structure, including, for example, support member 150 and support element 160, enables the use of a sensing element 140 having a smaller average diameter than previously possible. In several embodiments, for example, a wiring having an average diameter no greater than approximately 10 μm formed from a platinum-iridium alloy was used. Such a small average diameter wire (with a corresponding higher per unit length resistance than larger diameter wires) lends itself well to reducing the required operating current (which is very desirable in portable applications), and thus the required power levels.

Figure 2D:
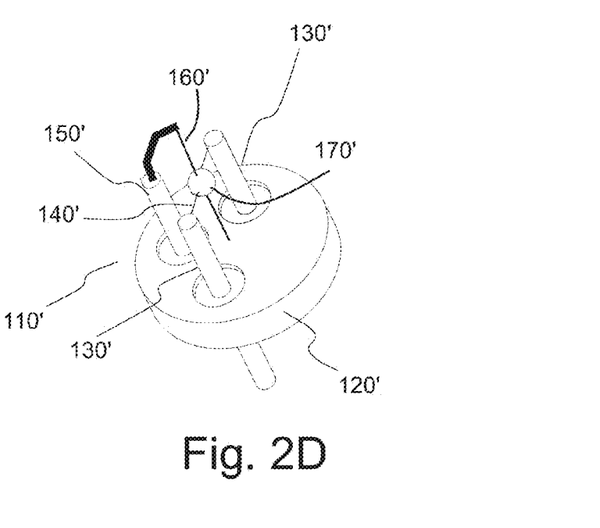
FIG. 2D illustrates a perspective view another embodiment of a detector assembly wherein an extending supporting element provides support for a conductive element of a sensing element.

The support elements hereof can be anchored to any suitable anchorage within the sensors hereof and can extend at virtually any angle. For example, in another representative embodiment, FIG. 2D illustrates an embodiment of a detector assembly 110' which includes a base 120' to which two electrically conductive contact members 130' are attached. A sensing conductive element 140' is connected between contact members 130'. Detector assembly 110' further includes a support member 150' connected to base 120'. A support member or element 160' in the form of, for example, a wire, a ribbon, a rod or other suitable support structure or material extends between support member 150' and base 120', through a catalyst support member 170', to provide support for conductive element 140.

Use of such small average diameter or small average cross-sectional area sensing conductive elements was not previously possible because, as described above, previously available support mechanisms for such fragile elements drew or conducted away too much heat to make the use of such elements beneficial. Indeed, robust sensing elements (or detectors) with generally spherical beads as catalyst support members that are smaller than 500 µm in average diameter were not previously available with a sensing conductive element or wire of relatively small average diameter (for example, having an average diameter of less than 20 µm, having an average diameter of less than 15 µm, having an average diameter less than 12.5 µm, or, in certain embodiments, having an average diameter of no greater than approximately (that is, within 10% of) 10 µm). In a number of embodiments, the volume of support catalyst member 170 is no greater than a sphere having a diameter of 500 µm, no greater than the volume of a sphere having a diameter no greater than 440 µm, no greater than the volume of a sphere having a diameter of 400 µm, or no greater than the volume of a sphere having a diameter of 300 µm. As set forth above, the volume (V) of a sphere is provided by the formula: $V=(4/3)*\pi*(diameter/2)^3$. In general, catalyst support members formed as a ceramic bead are formed by dipping, and the resultant ceramic bead is generally spherical or cylindrical. However, generally any shape of catalyst support member can be used.

Industry safety performance standards have been put in place to ensure that the products offered are in fact robust enough to survive a drop or impact. Standards from the Mine Safety and Health Administration (MSHA; ex. ASTP2015—Drop Test of Portable Methane Detectors), CSA International (a provider of product testing and certification services; ex. C22.2 No. 152-M1984 (2001) requirement 6.6.2), and ATEX (setting for standards in the European Union; ex. EN 61779-1:2000 requirement 4.4.14) all include a drop test, such as a 3 foot (1 m) drop test. While many products and designs on the market today can meet those standards, customers are increasingly demanding better performance. Testing has shown that the sensors hereof, in which a sensing element is supported by an extending support element that is anchored at each end, exhibit significantly improved sensor durability as illustrated in Table 1.

TABLE 1

20 Instruments Dropped 18 Times Each
Passing Drop Test (%)

| Drop Height | Currently available sensor | Sensor with anchored support element 160 |
|---|---|---|
| 3 feet (1 meter) | 100% | 100% |
| 6 feet (2 meter) | 100% | 100% |
| 10 feet (3 meter) | 50% | 100% |
| 20 feet (6 meter) | 0% | 100% |

For the test results in Table 1, a drop was preformed three separate times, with the apparatus being released each time with a different side (surface) facing down at the time of release. A total of 18 drops were therefore required for rectangular shaped instruments. The currently available sensors tested included a 625 µm diameter bead supported with quartz wool packing and a 12.5 µm (platinum-rhodium) sensing conductive element. The sensors with anchored support element 160 hereof tested included a 440 µm bead for catalyst support member 170, a 25 µm platinum-tungsten wire for support element 160, a 10 µm (platinum-iridium) for sensing conductive element 140. As set forth in Table 1, not only did sensors hereof pass 3-foot (1 meter) drop tests, sensors hereof passed drop tests of 6 feet (2 meters), 10 feet (3 meters) and 20 fee (6 meters). Support element 160 thus increases durability while decreasing heat loss as compared to sensors including other support systems or support mechanisms.

In that regard, testing showed that supported sensing elements as described in FIGS. 2A through 2D efficiently used less power as compared to support mechanisms in previously available combustible gas sensors and were sufficiently small to not be significantly influenced by changes in ambient humidity or ambient pressure as illustrated by the data of Tables 2 and 3 (in which the abbreviation LEL represents lower explosion limit). Humidity was studied in the range of 10-90% relative humidity (RH) over a temperature range of 25° C. to 40° C.

TABLE 2

| Support Method | Additional Power |
|---|---|
| 0.010 Ceramic Rod | 20% |
| Wool Packing | 10% |
| 0.002 Platinum wire | 5% |
| 0.001 Platinum-Tungsten Wire | 1% |

TABLE 3

| Bead Diameter (µm) | Humidity Response |
|---|---|
| 750 | −10% LEL |
| 625 | −5% LEL |
| 500 | −3% LEL |
| 440 | −1% LEL |

Figure 3A:
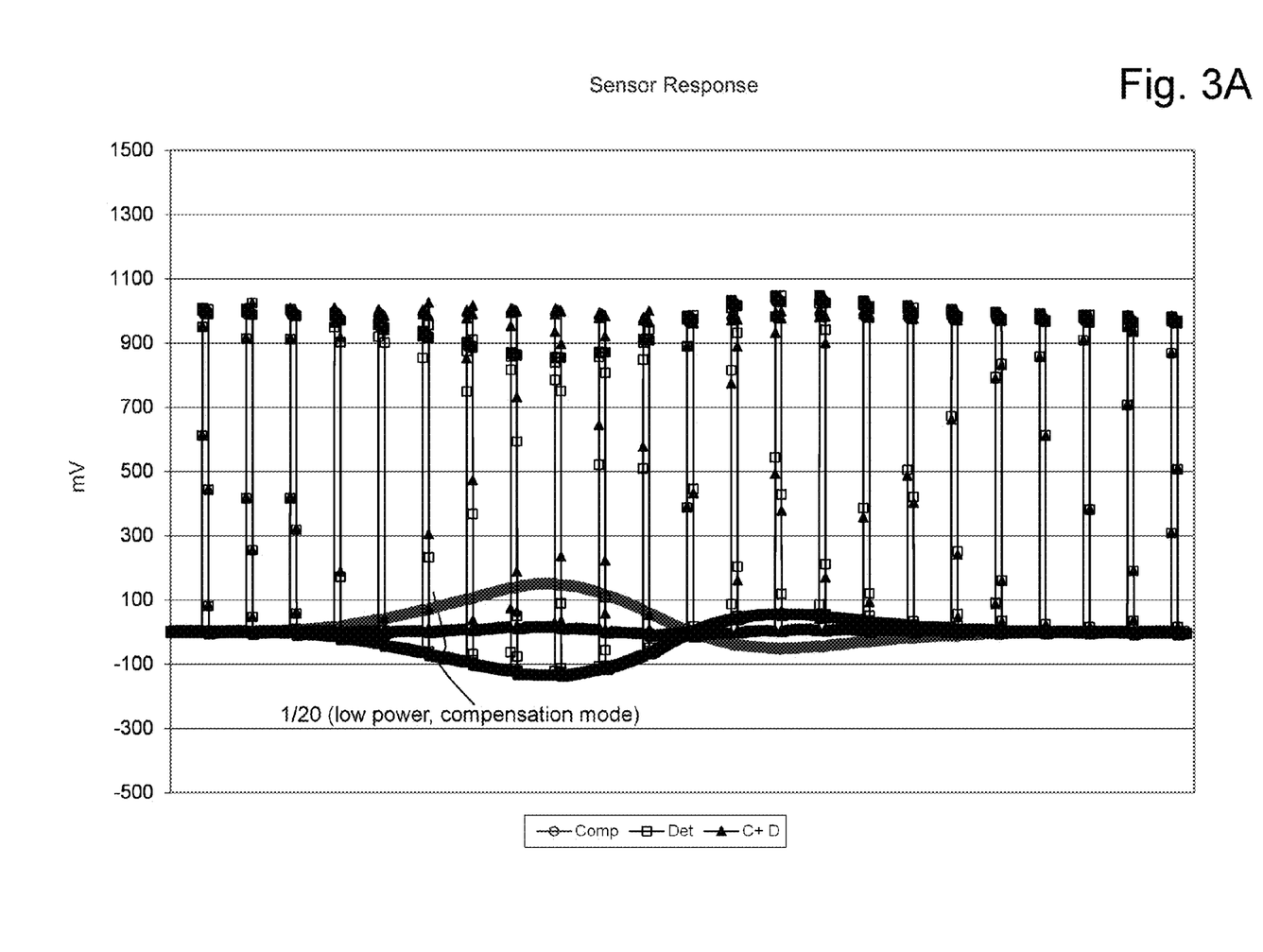
FIG. 3A illustrates sensor response to periodic inflow of 2.5% methane over a −30 to +50° C. temperature range.
Figure 3B:
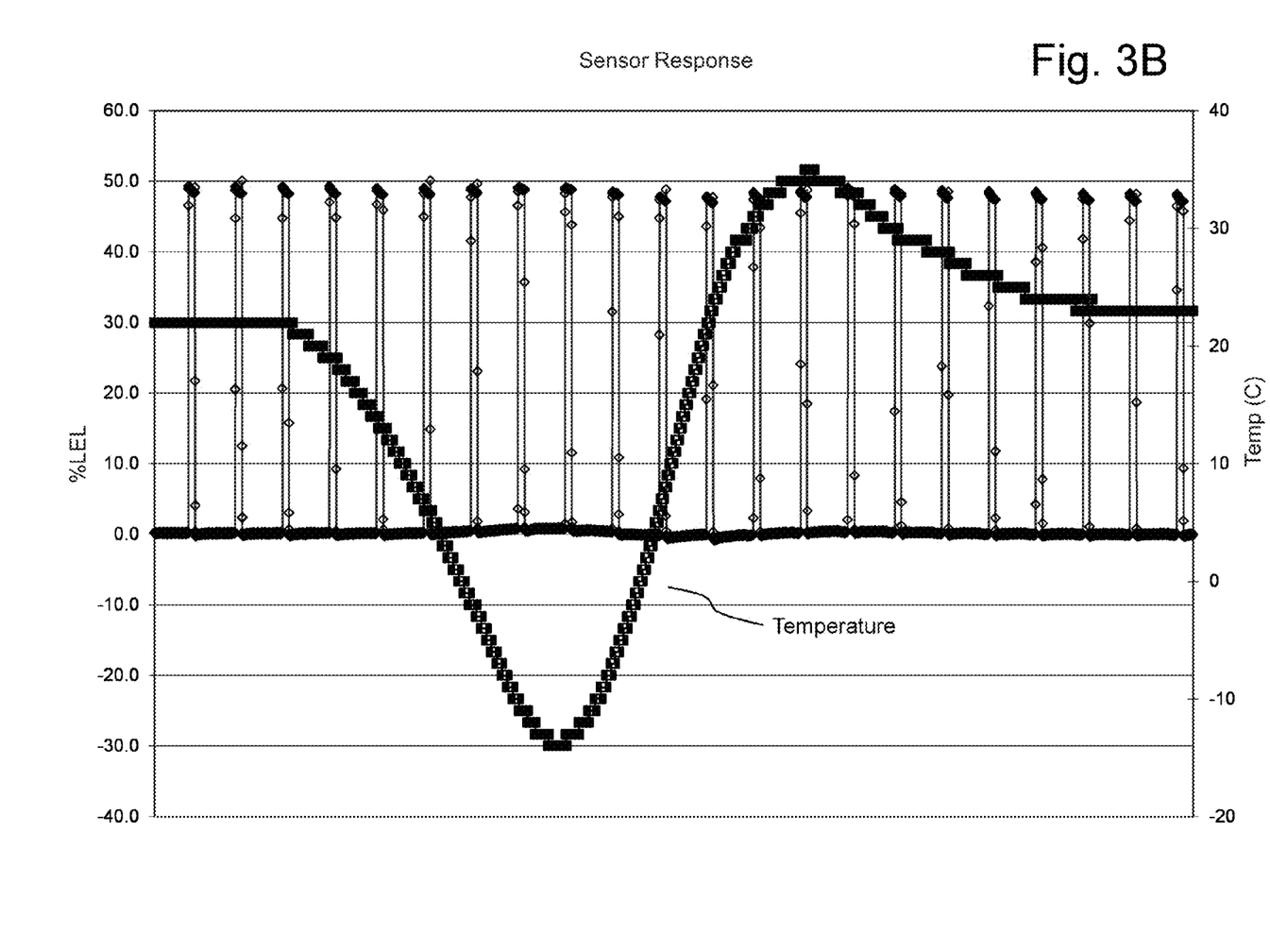
FIG. 3B illustrates sensor response calibrated to 50% LEL, as well as temperature variance as a function of time.

Subsequent to humidity and temperature testing, testing was conducted to study the ability of the sensing elements to detect changes in temperature as a result of the presence of combustible gas and as a result ambient temperate effects. Because sensing conductive element 130 was chosen to have ample thermal sensitivity, both effects were prevalent. FIG. 3A illustrates signal responses to periodic inflow/spikes of 2.5% methane over a temperature range of −30 to +50° C. The trace labeled 1/20 (low power, compensation mode) sets forth data for a sensing element or detector operated at 1/20 the power of an active sensing element or detector, thereby providing a "temperature compensating" function as described above. FIG. 3B illustrates sensor response calibrated to 50% LEL. FIG. 3B also sets forth how temperature was varied over the time of the study.

Testing was also conducted wherein the sensing elements of detector assemblies 110 were operated at low currents (for example, as low as 1/20 of the normal operating current) to monitor the effect of changes in ambient temperature only. In such an operating mode, the sensing elements required only a few milliwatts to operate (see FIGS. 3A and 3B). The results of the testing indicated that the sensing elements of detector assemblies 110, when operated at low power (that is, sufficiently low power to reduce the catalytic activity of the sensing element, for example, to render the sensing element substantially or completely inactive with respect to combustible gas), can be used as a replacement for a compensating element. Since humidity and pressure effects are negligible and only wire chemistry temperature effects are significant in the sensing element, the need to match such sensing elements precisely is relaxed by an order of magnitude as compared to sensing element/compensating element pairs of currently available combustible gas sensors.

Figure 4:
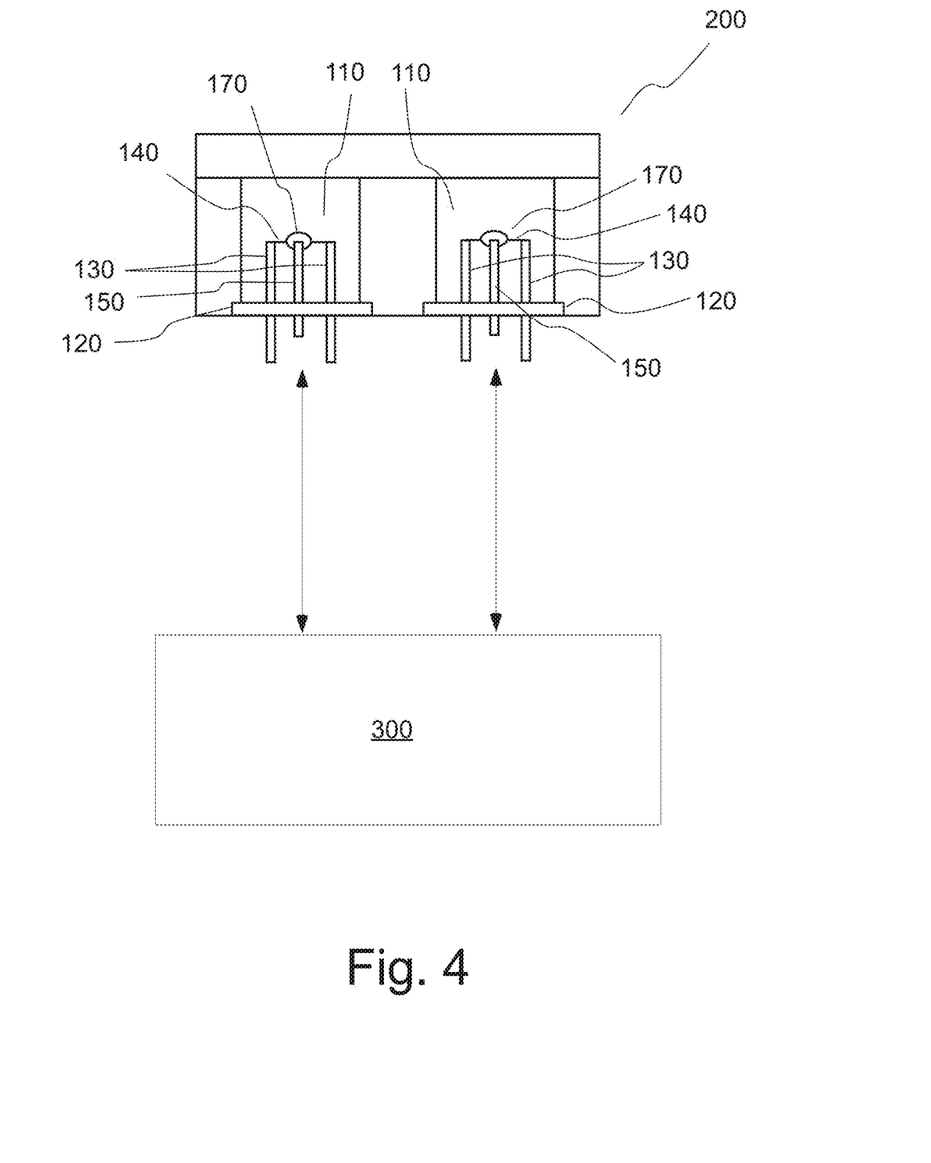
FIG. 4 illustrates a combustible gas sensor including two detector assemblies of FIG. 2B in electrical connection with control and measurement circuitry (illustrated as a box).

Sensor or sensor assemblies 200 (see FIG. 4) were made which included two detector assemblies 110, but no compensator. During normal operation, only one of the sensing elements/detectors is, for example, operated to be catalytically active (that is, at high power/high temperature) at one time. The other sensing element/detector is operated at low power/low temperature (for example, such that it is substantially or completely catalytically inactive with respect to combustible gas) and thus acts as the thermal compensator (that is, a compensator for the effects of ambient temperature change). Sensor 200 required less than 100 mW to operate. Since each sensing element can be operated independently, the sensor life can be essentially doubled as compared to currently available sensors.

Because no compensator or compensating element is required, and elements are not required to be matched, sensor 200 operates at nearly half the power required as compared to currently available combustible gas sensors. Moreover, sensor 200 can potentially operate twice as long as currently available combustible gas sensors, while being produced at substantially less cost (as a separate compensating element does not have to be produced and matched).

In other embodiments, an additional sensing element can be provided. An operating mode for using thermal conductivity to measure high gas concentrations can also be included by which intermediate lower power levels are selected to determine the gas concentration. Further, various electronic systems and methods can be used to switch operation of the sensing element or otherwise save power. For example, pulsing, pulse width modulation, or other power savings modes of operation can be provided to further reduce the required power.

The sensing elements of the sensor can be switched between a high power/high temperature active mode and a low power/low temperature inactive or compensating mode over a wide range of periods. In general, the period of cycling is limited (on the lower end) by the amount of time required to achieve equilibrium or steady state operation. Periods as low as, for example, 20 seconds were possible with the sensing elements tested. Much longer periods (for example, hours days, weeks, months or longer) are also possible. Electronic circuitry 300 (see FIG. 4), which is in electrical connection with contact posts 130 of each of detector assemblies 110, can effect automatic periodic switching between sensing element modes. Alternatively, switching between modes can be effected after a manually initiated or controlled event such as a power off/power on (or power cycling) procedure or event.

Figure 5:
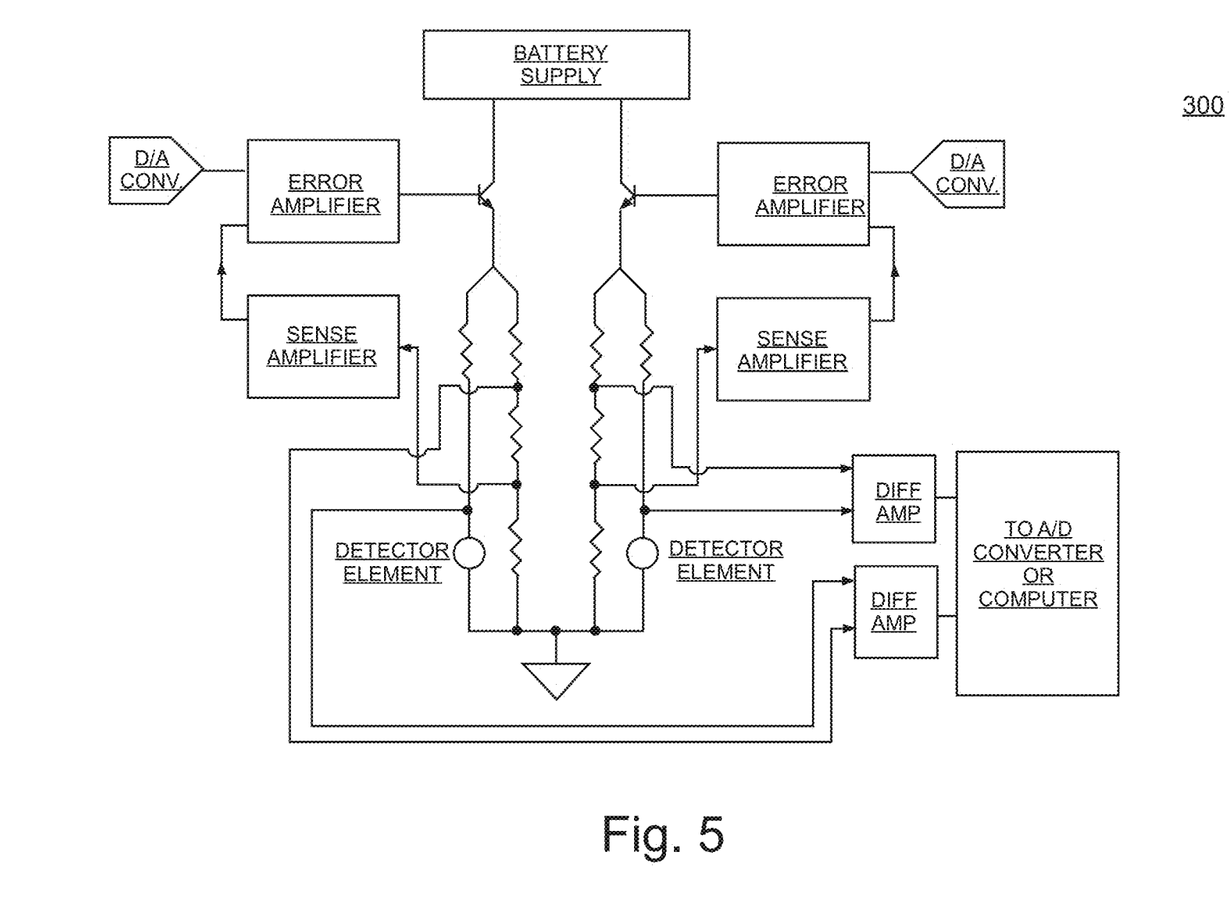
FIG. 5 illustrates a schematic diagram of an embodiment of control and measurement circuitry for use in connection with, for example, the combustible gas sensor of FIG. 3.

U.S. Pat. Nos. 4,533,520 and 5,780,715 disclose systems and method to, for example, balance bridges electronically and to operate sensing elements independently. Such systems and methods can, for example, be incorporated in circuitry 300. FIG. 5 illustrates a schematic drawing of electronic (for example, control and/or measurement) circuitry 300. In electronic circuitry 300, the Digital/Analog (D/A) converters set the power level to the sensing elements/detectors. Setting a low target value ($1/20^{th}$) causes the sensing or detector element to act as a temperature compensator as described above. Each sensing or detector element is electrically connected in an independent bridge circuit, and is read by a processor/computer. The processor computes the relative responses and the final gas response.

The devices, systems and/or methods described herein can be used in connection with a variety of types of combustible gas sensors. For example, such devices, systems and/or methods can be used in connection with Micro-Electro-Mechanical Systems (MEMS), thin/thick film system, or other suitable micro- or nanotechnology systems such as, for example, described in U.S. Pat. No. 5,599,584 and/or U.S. Pat. No. 6,705,152.

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A combustible gas sensor comprising a first sensing element and a second sensing element, the first sensing element comprising a first catalyst support member having a volume less than a sphere having a diameter of 500 μm and upon which a catalyst is supported, the second sensing element comprising a second catalyst support member having a volume less than a sphere having a diameter of 500 μm and upon which a catalyst is supported, and electronic circuitry that is adapted to cycle between a first mode in which the first sensing element is operated in a higher power mode and the second sensing element is operated in a lower power mode and a second mode in which the second sensing element is operated in a higher power mode and the first sensing element is operated in a lower power mode.

2. The combustible gas sensor of claim 1 wherein in the first mode the second sensing element is used to compensate for ambient temperature changes and in the second mode the first sensing element is used to compensate for ambient temperature changes.

3. The combustible gas sensor of claim 1 wherein the first sensing element comprises a first conductive element having an average diameter less than 20 μm in operative connection with the first catalyst support member and in electrical connection with the electronic circuitry, the combustible gas sensor further comprising a first support element having a first anchored end and a second anchored end and an extending intermediate section between the first anchored end and the second anchored end, the extending intermediate section providing support for the first conductive element and the first catalyst support member, and wherein the second sensing element comprises a second conductive element having an average diameter less than 20 μm in operative connection with the second catalyst support member and in electrical connection with the electronic circuitry, the combustible gas sensor further comprising a second support element having a first anchored end and a second anchored end and an extending intermediate section between the first anchored end and the second anchored end, the extending intermediate section of the second support element providing support for the second conductive element and the second catalyst support member.

4. The combustible gas sensor of claim 3 wherein the first support element exhibits a first quotient calculated by dividing a tensile strength thereof in units of pounds per square inch or psi by a thermal conductivity thereof in units of watts/cm/° C. of at least 250,000, and the second support element exhibits a second quotient calculated by dividing tensile strength thereof in units of pounds per square inch or psi by a thermal conductivity thereof in units of watts/cm/° C. of at least 250,000.

5. The combustible gas sensor of claim 4 wherein the first sensing element has an average diameter less than 12.5 μm, and the second sensing element has an average diameter less than 12.5 μm.

6. The combustible gas sensor of claim 4 wherein the first sensing element has an average diameter no greater than approximately 10 μm, and the second sensing element has an average diameter no greater than approximately 10 μm.

7. The combustible gas sensor of claim 3 wherein the first support element pass through at least a portion of the first catalyst support member, and the second support element pass through at least a portion of the second catalyst support member.

8. The combustible gas sensor of claim 3 wherein the first support element comprises an alloy of at least one of tungsten, nickel, molybdenum or titanium with at least one of platinum, palladium, rhodium or iridium and the second support element comprises an alloy of at least one of tungsten, nickel, molybdenum or titanium with at least one of platinum, palladium, rhodium or iridium.

9. The combustible gas sensor of claim 3 wherein the first support element and the second support element each comprises a platinum-tungsten alloy.

10. The combustible gas sensor of claim 3 wherein the first support element has an average diameter in the range of approximately 0.0005 inches to approximately 0.0025 inches and the second support element has an average diameter in the range of approximately 0.0005 inches to approximately 0.0025 inches.

11. The combustible gas sensor of claim 3 wherein the first conductive element has an average diameter no greater than approximately 10 μm and the second conductive element has an average diameter no greater than approximately 10 μm.

12. The combustible gas sensor of claim 1 wherein the electronic circuitry is adapted to periodically switch between the first mode and the second mode.

13. The combustible gas sensor of claim 1 wherein the electronic circuitry is adapted to switch between the first mode and the second mode upon a manually controlled event.

14. The combustible gas sensor of claim 13 wherein the manually controlled event comprises a power on event.

15. A method of operating a combustible gas sensor which comprises a first sensing element and a second sensing element, the first sensing element comprising a first catalyst support member having a volume less than a sphere having a diameter of 500 μm and upon which a catalyst is supported, the second sensing element comprising a second catalyst support member having a volume less than a sphere having a diameter of 500 μm and upon which a catalyst is supported, comprising: cycling between a first mode in which the first sensing element is operated in a higher power mode and the second sensing element is operated in a lower power mode and a second mode in which the second sensing element is operated in a higher power mode and the first sensing element is operated in a lower power mode.

16. The method of claim 15 wherein in the first mode the second sensing element is used to compensate for ambient temperature changes and in the second mode the first sensing element is used to compensate for ambient temperature changes.

\* \* \* \* \*